(12) United States Patent
Eicher et al.

(10) Patent No.: US 7,629,496 B2
(45) Date of Patent: Dec. 8, 2009

(54) PROCESS FOR THE MANUFACTURE OF 1,1,1,3,3-PENTAFLUOROPROPANE

(75) Inventors: Johannes Eicher, Sehnde (DE); Stefan Mross, Brussels (BE)

(73) Assignee: Solvay (Societé Anonyme), Brussels (BE)

( * ) Notice: Subject to any disclaimer, the term of this patent is extended or adjusted under 35 U.S.C. 154(b) by 0 days.

(21) Appl. No.: 12/282,386

(22) PCT Filed: Mar. 22, 2007

(86) PCT No.: PCT/EP2007/052769

§ 371 (c)(1),
(2), (4) Date: Sep. 10, 2008

(87) PCT Pub. No.: WO2007/110377

PCT Pub. Date: Oct. 4, 2007

(65) Prior Publication Data

US 2009/0062577 A1   Mar. 5, 2009

(30) Foreign Application Priority Data

Mar. 24, 2006   (EP) .................................. 06111713

(51) Int. Cl.
C07C 17/23   (2006.01)
C07C 19/08   (2006.01)

(52) U.S. Cl. ...................................... 570/176; 570/134
(58) Field of Classification Search .................. 570/176
See application file for complete search history.

(56) References Cited

U.S. PATENT DOCUMENTS

| | | | | |
|---|---|---|---|---|
| 5,663,464 A | * | 9/1997 | Okamoto et al. | 570/175 |
| 5,728,904 A | * | 3/1998 | Van Der Puy et al. | 570/176 |
| 5,821,392 A | * | 10/1998 | Aoyama et al. | 570/176 |
| 5,945,573 A | * | 8/1999 | Nappa et al. | 570/175 |
| 6,060,628 A | * | 5/2000 | Aoyama et al. | 570/134 |

FOREIGN PATENT DOCUMENTS

| | | |
|---|---|---|
| EP | 0522639 A1 | 1/1993 |
| JP | 09067281 A | 3/1997 |
| WO | WO9833756 A | 8/1998 |

OTHER PUBLICATIONS

PCT International Search Report dated May 18, 2007 for International Application No. PCT/EP2007/052769 (2 pp.).

* cited by examiner

*Primary Examiner*—Brian J Davis
(74) *Attorney, Agent, or Firm*—Beatrice C. Ortego

(57) ABSTRACT

A process for the manufacture of 1,1,1,3,3-pentafluoropropane, which comprises reacting 1,1,1,3,3,3-hexafluoropropane with a source of hydrogen.

10 Claims, No Drawings

PROCESS FOR THE MANUFACTURE OF 1,1,1,3,3-PENTAFLUOROPROPANE

CROSS-REFERENCE TO RELATED APPLICATIONS

This application is a U.S. national stage application under 35 U.S.C. §371 of International Application No. PCT/EP2007/052769, filed Mar. 22, 2007, which claims priority to European Application No. EP06111713.1, filed Mar. 24, 2006, all of these applications being herein incorporated by reference in their entirety for all purposes.

The present invention relates to a process for the manufacture of 1,1,1,3,3-pentafluoropropane. 1,1,1,3,3-pentafluoropropane is useful amongst others as constituent of blowing agents for polyurethane foams in compositions with 1,1,1,3,3-pentafluorobutane.

The invention allows for efficient manufacture of 1,1,1,3,3-pentafluoropropane.

The invention concerns a process for the manufacture of 1,1,1,3,3-pentafluoropropane, which comprises reacting 1,1,1,3,3,3-hexafluoropropane with a source of hydrogen. The 1,1,1,3,3,3-hexafluoropropane is generally reacted with a source of hydrogen under conditions maximizing production of 1,1,1,3,3-pentafluoropropane.

In the process according to the invention the reaction is generally carried out in the presence of a hydrogenation catalyst. This catalyst is preferably selected from metals of Group VIII of the periodic table of elements, more particular it is selected from Pd, Pt, Rh, Ru, Ni and Ir. Pd is preferred.

The catalyst is preferably supported. Support can be active carbon, alumina, fluorinated alumina, $LiAl_5O_8$, or fluorinated derivative thereof.

The source of hydrogen is preferably hydrogen gas. The molar ratio of hydrogen (or hydrogen equivalent) to 1,1,1,3,3,3-hexafluoropropane is generally from 1 to 5, often from 1.5 to 3 and preferably from 1.5 to 2.

In the process according to the invention the reaction can suitably be carried out in the gas phase. In that case the reaction is generally carried out at a temperature from 0 to 500° C., often the temperature is from 50 to 250° C. and preferably from 80° C. to 200° C. In that case, the reaction is generally carried out at a pressure from 1 to 20 bar, often the pressure is from 2 to 10 bar and preferably from 1.5 to 5 bar.

In another embodiment, the reaction is carried out in the liquid phase. In that case the reaction is generally carried out at a temperature from 50 to 250° C., often the temperature is from 70 to 200° C. and preferably from 80° C. to 150° C. In that case, the reaction is generally carried out at a pressure from 1 to 60 bars, often the pressure is from 5 to 50 bars and preferably from 10 to 40 bars.

In the process according to the invention the reaction can suitably be carried out continuously. It can also be carried out batchwise.

In a particular embodiment, the process according to the invention comprises
(a) reacting 1,1,1,3,3,3-hexachloropropane with hydrogen fluoride to form a reaction product comprising 1,1,1,3,3,3-hexafluoropropane and optionally starting materials and intermediates
(b) separating 1,1,1,3,3,3-hexafluoropropane from the reaction product and optionally recycling starting materials and intermediates to step (a)
(c) reacting 1,1,1,3,3,3-hexafluoropropane obtained in step (b) with a source of hydrogen according to the process of anyone of claims 1 to 9.

The manufacture of 1,1,1,3,3,3-hexafluoropropane is described for example in EP-A-522639 in the name of the applicant, the disclosure of which is incorporated by reference into the present application. According to EP-A 522639, 1,1,1,3,3,3-hexafluoropropane can be prepared from 1,1,1,3,3,3-hexachloropropane (which in turn preferably is prepared from vinylidene chloride and tetrachloromethane) in a liquid phase reaction with HF, in the presence of a catalyst. The catalyst preferably favors the substitution of a chlorine atom by a fluorine atom. Suitable catalysts are for example selected from compounds of metals of groups IIIa, IVa and IVb, Va and Vb, and VIb of the periodic table. Compounds of titanium, tantalum, molybdenum, boron, tin and antimony are preferred, especially those of tin and antimony. Especially preferred are the chlorides, fluorides and chlorofluorides of the metals. Generally, the fluorination reaction is performed between 50 and 150° C. The pressure, often between 2 and 50 bar, is such that the reaction mixture is kept in the liquid phase. The catalyst quantity is very variable. Generally, it is at least 0.005 mole of catalyst per mole of 1,1,1,3,3,3-hexachloropropane, and often, it is not higher than 0.6 mole per mole of 1,1,1,3,3,3-hexachloropropane. The ratio between HF and 1,1,1,3,3,3-hexachloropropane is generally at least 4, and often will not be higher than 20.

The example here after is intended to illustrate the invention without limiting it.

EXAMPLE

In a stainless steel reactor a catalyst comprising 10% Pd on active carbon is charged. Hydrogen gas is introduced continuously at a pressure of 2 bar and a temperature of 200° C. 1,1,1,3,3,3-hexafluoropropane is then introduced continuously to obtain a molar ratio H2/1,1,1,3,3,3-hexafluoropropane of 2 to 1. The reactor effluents are liquefied in a cold trap. The analysis of the contents of the cold trap shows formation of 1,1,1,3,3-pentafluoropropane.

The invention claimed is:

1. A process for the manufacture of 1,1,1,3,3-pentafluoropropane, which comprises reacting 1,1,1,3,3,3-hexafluoropropane with a source of hydrogen.

2. The process of claim 1, wherein the reaction is carried out in the presence of a hydrogenation catalyst.

3. The process of claim 1, wherein the catalyst is selected from the group consisting of Pd, Pt, Rh, Ru, Ni, and Ir.

4. The process of claim 1, wherein the source of hydrogen is hydrogen gas.

5. The process of claim 1, wherein the reaction is carried out in the gas phase.

6. The process of claim 5, wherein the reaction is carried out at a temperature from 0 to 500° C.

7. The process of claim 5, wherein the reaction is carried out at a pressure from 1 to 20 bar.

8. The process of claim 1, wherein the reaction is carried out in the liquid phase.

9. The process of claim 1, wherein the reaction is carried out continuously.

10. A process for the manufacture of 1,1,1,3,3-pentafluoropropane, said process comprising:
(a) reacting 1,1,1,3,3,3-hexachloropropane with hydrogen fluoride to form a reaction product comprising 1,1,1,3,3,3-hexafluoropropane and optionally starting materials and intermediates;
(b) separating 1,1,1,3,3,3-hexafluoropropane from the reaction product and optionally recycling starting materials and intermediates to step (a); and
(c) reacting 1,1,1,3,3,3-hexafluoropropane obtained in step (b) with a source of hydrogen.

* * * * *